(12) United States Patent
Schoeler

(10) Patent No.: US 10,401,613 B2
(45) Date of Patent: Sep. 3, 2019

(54) ASSEMBLY OF AN ENDOSCOPE HAVING A TUBE COMPRISING SHAPE-MEMORY MATERIAL FOR THE CLAMP-MOUNTING OF OPTICAL ELEMENTS

(71) Applicant: OLYMPUS WINTER & IBE GMBH, Hamburg (DE)

(72) Inventor: Uwe Schoeler, Hoisdorf (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 0 days.

(21) Appl. No.: 15/679,424

(22) Filed: Aug. 17, 2017

(65) Prior Publication Data

US 2017/0363856 A1 Dec. 21, 2017

Related U.S. Application Data

(63) Continuation of application No. PCT/EP2016/052060, filed on Feb. 1, 2016.

(30) Foreign Application Priority Data

Feb. 25, 2015 (DE) ........................ 10 2015 203 357

(51) Int. Cl.
*G02B 7/02* (2006.01)
*G02B 23/24* (2006.01)
(Continued)

(52) U.S. Cl.
CPC ...... *G02B 23/2476* (2013.01); *A61B 1/00096* (2013.01); *A61B 1/00188* (2013.01);
(Continued)

(58) Field of Classification Search
CPC .......... G02B 21/00; G02B 21/02; G02B 7/00; G02B 7/02; G02B 23/2476; G02B 7/021;
(Continued)

(56) References Cited

U.S. PATENT DOCUMENTS 5,607,435 A 3/1997 Sachdeva et al.
6,324,742 B1 12/2001 Odanaka
(Continued)

FOREIGN PATENT DOCUMENTS

DE 3007307 A1 7/1981
DE 19732991 A1 2/1999
(Continued)

OTHER PUBLICATIONS

Brenner, Walter, "Choosing the Right Epoxy for Optical Applications," www.photonics.com. (Year: 2012).*
(Continued)

*Primary Examiner* — William Choi
(74) *Attorney, Agent, or Firm* — Scully, Scott, Murphy & Presser, P.C.

(57) ABSTRACT

An optical assembly for an endoscope, the optical assembly including: an objective tube; and at least one optical element held in the objective tube; wherein the objective tube comprises at least one region acting as a clamping mount for the at least one optical element, and the at least one region of the objective tube acting as the clamping mount is at least sectionally formed of a shape-memory material.

12 Claims, 4 Drawing Sheets

(51) Int. Cl.
*A61B 1/00* (2006.01)
*F16B 1/00* (2006.01)

(52) U.S. Cl.
CPC ............ *G02B 7/021* (2013.01); *G02B 23/243* (2013.01); *F16B 1/0014* (2013.01); *G02B 23/2446* (2013.01)

(58) Field of Classification Search
CPC .............. G02B 23/243; G02B 23/2446; A61B 1/00163; F16B 1/2446
USPC ................................... 359/65–661, 811, 819
See application file for complete search history.

(56) References Cited

U.S. PATENT DOCUMENTS 6,398,723 B1 6/2002 Kehr et al.
2012/0176613 A1 7/2012 Marple et al.

FOREIGN PATENT DOCUMENTS

| DE | 102008038619 B3 | 2/2010 |
|---|---|---|
| JP | S63-208018 A | 8/1988 |
| JP | 2006-133695 A | 5/2006 |

OTHER PUBLICATIONS

"Nitinol Specifcation Guidelines," www.j.mmedical.com/resources/120/Nitinol-Specification-Guidelines.html (Year: 2018).*
International Search Report dated Apr. 22, 2016 issued in PCT/EP2016/052060.
Japanese Office Action dated Feb. 26, 2019 in Japanese Patent Application No. 2017-545364.

* cited by examiner

Fig. 2
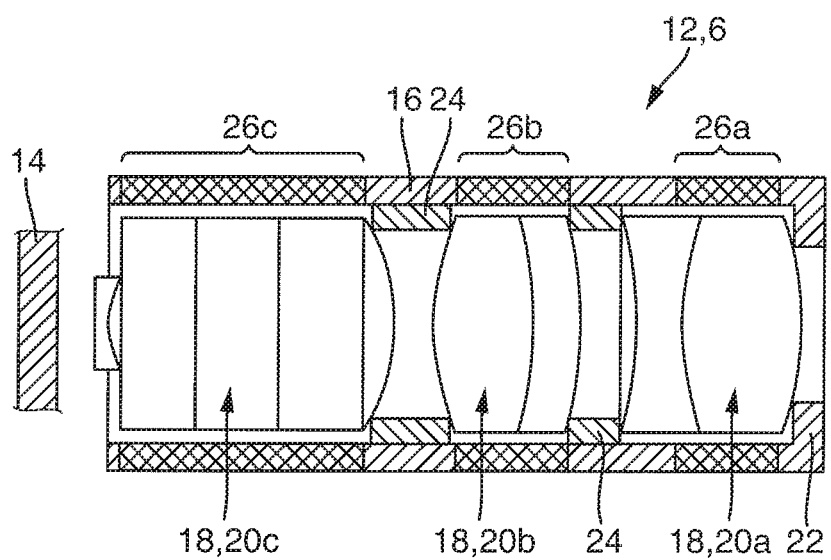
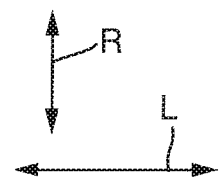

ASSEMBLY OF AN ENDOSCOPE HAVING A TUBE COMPRISING SHAPE-MEMORY MATERIAL FOR THE CLAMP-MOUNTING OF OPTICAL ELEMENTS

CROSS-REFERENCE TO RELATED APPLICATION

The present application is a continuation of PCT/EP2016/052060 filed on Feb. 1, 2016, which is based upon and claims the benefit to DE 10 2015 203 357.0 filed on Feb. 25, 2015, the entire contents of each of which are incorporated herein by reference.

BACKGROUND

Field

The present application relates to an optical assembly of an endoscope comprising an objective tube and at least one optical element held in the objective tube. Moreover, the present application relates to an endoscope comprising an optical assembly, a method for producing an optical assembly, and the use of a shape-memory material.

Prior Art

An investigated area in front of a distal end of the endoscope shaft is observed with an endoscope objective. The endoscope objective is typically sealed with a protective window against the exterior. The endoscope objective depicts the investigated area on an image sensor. Alternatively, the image is projected by relay lenses to the proximal region of the endoscope. The image sensor or eyepiece is located there for directly observing the investigated area. With flexible endoscopes, the optical imaging occurs on a flexible bundle of optical fibers.

The endoscope objective and the relay lenses will be generally termed optical assemblies of the endoscope in the following. They normally comprise several lenses or lens groups that are arranged sequentially in the longitudinal direction of the endoscope and/or are held in an objective or system tube.

DE 10 2008 038 619 B3 discloses an endoscope objective with three lens groups that are accommodated with circumferential play in an objective tube. The objective tube comprises an interior flange that serves as a stop for the lens groups in the longitudinal axial direction. In the radial direction, the lenses are fixed by adding a low-viscosity adhesive in the gap between the lens, or respectively lens group, and objective tube through holes in the objective tube. After the adhesive cures, there is a secure connection between the lens group and the objective tube.

SUMMARY

It is an object to present an optical assembly of an endoscope, an endoscope comprising an optical assembly, a method for producing an optical assembly, and the use of a shape-memory material, wherein the optical assembly satisfies stringent optical requirements.

Such object can be solved with an optical assembly of an endoscope comprising an objective tube and at least one optical element held in the objective tube, wherein the objective tube comprises at least one region that acts as a clamping mount for the optical element, wherein the region of the objective tube that acts as a clamping mount is manufactured at least sectionally from a shape-memory material.

In the context of the present description, an "objective tube" should be understood as a system tube.

The present application contemplates the following considerations: The tolerances of the individual components in the production of optical assemblies, such as endoscope objectives or relay lenses, are reaching the limits of technical feasibility, and they are still too large to satisfy increasing optical requirements, especially with regard to high-resolution imaging (HD, 4K and successor technologies). A press-fit of the optical element in the region of the objective functioning as a clamping mount yields the possibility (which is recognized herein) of satisfying these demands on the mechanical side with regard to tolerances, production precision and the adjustment precision of the optical elements. The optical elements, such as lenses or lens groups, are centered with high precision on the optical axis of the optical system. This effect is achieved because the shape-memory material can exert an even pressure on the optical element which acts from all sides.

According to one embodiment, the region of the objective tube acting as a clamping mount can fully enclose the optical element along a circumference of the objective tube and moreover can be made, at least partially, from the shape-memory material.

The circumference of the objective tube is viewed in a plane perpendicular to the optical axis of the optical system, or respectively perpendicular to the central longitudinal axis of the objective tube.

The optical element does not necessarily need to fully contact the objective tube along its circumference. The optical element can be specifically held at individual points that can be evenly distributed along the circumference of the optical element in the region of the objective tube functioning as a clamping mount. This type of clamping holder can allow the optical element to be accommodated free of play, precisely and specifically in the clamping holder provided by the objective tube.

According to another embodiment, at least one first optical element and one second optical element can be provided, wherein the first optical element can be held in a first region of the objective tube functioning as a clamping mount for the first optical element, and the second optical element can be held in a second region of the objective tube functioning as a clamping mount for the second optical element, and wherein the objective tube can comprise a deformable transition region between the first region and the second region.

In the context of the present description, "deformable transition region" means that this transition region is easily deformable plastically or elastically, or respectively is mechanically softer than the neighboring adjacent regions, or respectively sections of the objective tube. Spring elements can be provided as the transition region. The transition region can be formed from a metal or plastic.

Such features can make it possible to accommodate different size and different shape optical elements free of play, securely and reliably in the objective tube. The shape-memory material can be locally, i.e., within each individual region, able to optimally fit snugly against the optical element accommodated, or respectively held there and securely hold it.

In an development of the optical unit, the first region can have a first cross-section, such as a first diameter, and the second region can have a second cross-section different therefrom, such as a second diameter, wherein the deformable transition region can create a transition from the first cross-section to the second cross-section, such as a transition from the first diameter to the second diameter between the first and second region.

Different shapes of the optical elements that require a different cross-section, be it in size or shape, can be accommodated in the optical assembly according to the aforementioned embodiment. The same holds true, for example, for different sized lenses that have different sized diameters. The individual regions of the objective tube can be arranged relative to each other such that the optical elements accommodated therein are held precisely on a common optical axis. Different clamping forces can be exerted in different regions on the optical elements held therein.

According to another embodiment, at least one region of the objective tube functioning as a clamping mount can have a trained shape which is polygonal viewed in the cross-section of the objective tube, wherein a deformed shape of the objective tube can be circular, at least in the region functioning as a clamping mount.

In the context of the present description, a "trained shape" is the shape of the shape-memory material "remembered" by the material when it is heated to a temperature above the memory temperature. A "deformed shape" is the shape that the material assumes by being deformed below a critical temperature so that training of this shape does not occur. The shape-memory effect or memory effect occurs from the deformed shape to the trained shape when the memory temperature is exceeded.

The trained shape can be selected so that a clamping seat is provided between the optical element and the region of the objective tube functioning as a clamping mount. In other words, the trained shape can be accordingly selected so that a generated clamping force for the optical element to be received is neither too high nor too low.

The optical element can come to rest against the middle of one side of the aforementioned polygon. A triangular shape of the objective tube, at least in the region acting as a clamping mount for the optical element, can be used since a three-point seat constitutes a stable seat for the optical element in geometrical terms. A six-sided profile can be used since crossbars can be inserted for adjustment on the optical axis which can be removed after the clamping process.

According to another embodiment, the shape-memory material can be a shape-memory alloy and/or a shape-memory polymer.

A shape-memory alloy or memory material can be a nickel/titanium alloy such as a material known by the name of "Nitinol."

The optical element can be a lens. Moreover, lenses can be adhered to each other to form a lens group. The optical elements of the optical assembly can be held in the objective tube without any other holding measures such as adhesion, screwing, etc. The aforementioned features are applicable to all embodiments.

The object can be moreover solved with an endoscope comprising an optical assembly according to one or more of the aforementioned embodiments as an endoscope objective or relay lens, wherein the optical element can be a lens or lens group.

The endoscope objective can be suitable for high-resolution imaging since, with regard to the tolerances of the individual components of the optical assembly, the existing technical restrictions can be overcome.

Moreover, the object can be solved by a method for producing an optical assembly according to one or more of the aforementioned embodiments, wherein the method comprises:

providing an objective tube that at least comprises a region which functions as a clamping mount for the optical element and is at least sectionally manufactured from a shape-memory material, inserting at least one optical element into the region of the objective tube functioning as a clamping mount, and heating the at least one region of the objective tube functioning as a clamping mount to a temperature above a memory temperature of the used shape-memory material.

Moreover, the object can be solved by using a shape-memory material for manufacturing an objective tube of an optical assembly according to one or more of the aforementioned embodiments. The shape-memory material can be shape-memory metal or a shape-memory alloy, such as Nitinol.

Any advantages for the method and use can be similar as already noted with regard to the optical assembly of an endoscope, and they will, therefore, not be mentioned again.

Further features will become apparent from the description of embodiments together with the claims and the included drawings. Embodiments can fulfill individual characteristics or a combination of several characteristics.

BRIEF DESCRIPTION OF THE DRAWINGS

The embodiments are described below, without restricting the general concept, based on exemplary embodiments in reference to the drawings, wherein we expressly refer to the drawings with regard to the disclosure of all details that are not explained in greater detail in the text. In the Figures:

FIG. 2 illustrates a schematic longitudinal section of an optical assembly of an endoscope.

In the drawings, the same or similar types of elements and/or parts are provided with the same reference numbers so that a re-introduction is omitted.

DETAILED DESCRIPTION

Figure 1:
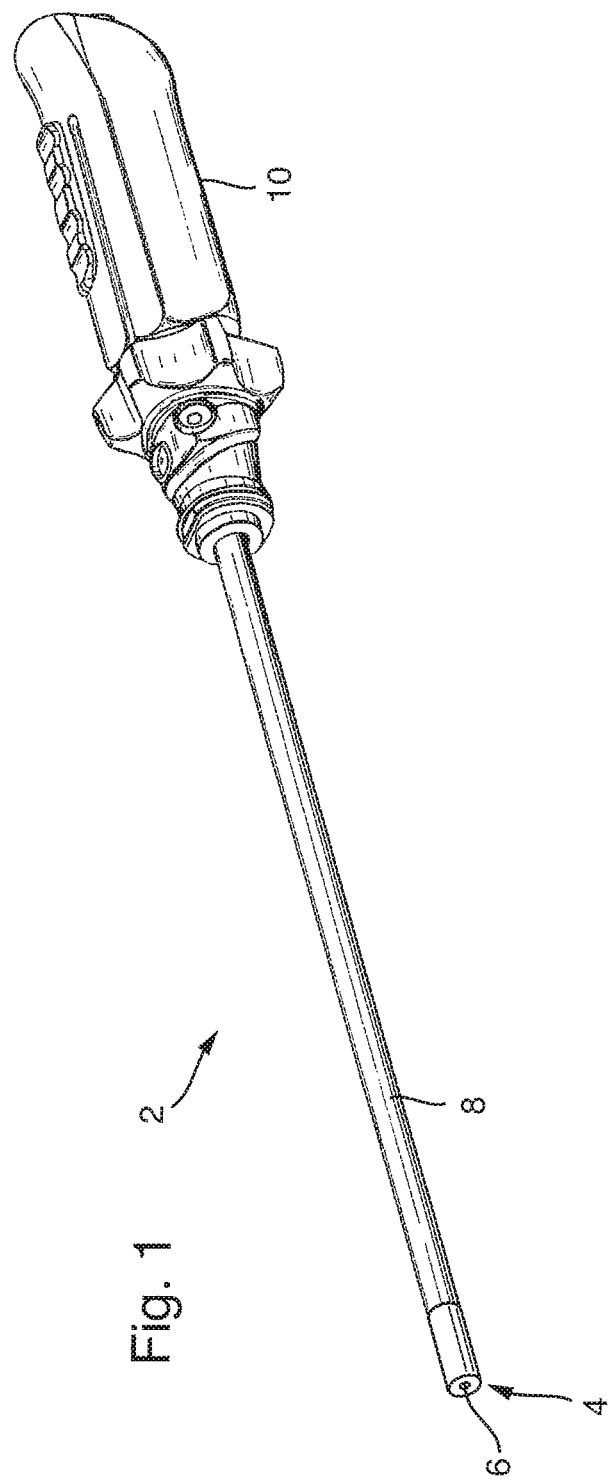
FIG. 1 illustrates a schematic, simplified and perspective view of an endoscope.

FIG. 1 shows a simplified, schematic and perspective representation of an endoscope 2, such as a rigid endoscope, on the distal end 4 of which there is an endoscope objective 6 that is arranged behind a protective disc (not shown). In a shaft 8 of the endoscope 2, there are moreover relay lenses (not shown) depending on the type of the endoscope 2. The endoscope objective 6 and these relay lenses form optical units of the endoscope 2. A proximal end of the endoscope 2 comprises a handle 10.

FIG. 2 shows a simplified and schematic longitudinal sectional view of an optical assembly 12 of endoscope 2, such as an endoscope objective 6. The endoscope objective 6 is arranged to the rear of the protective disc 14 on the distal end 4 of the shaft 8 of the endoscope 2. The optical assembly 12 comprises an objective tube 16 and at least one optical element 18 held in the objective tube 16, such as three optical elements 18, i.e., a proximal lens group 20a, a central lens group 20b and a distal lens group 20c. The lens groups 20a, 20b, 20c are only depicted as examples, and each consists of several individual lenses. An optical element is also individual lenses, prisms, etc.

The optical elements 18 are held in the objective tube 16 by a stop 22 at the proximal end of the objective tube 16, and by aperture tubes 24, which also function as a stop, between the lens groups 20a, 20b, 20c. In the radial direction R which runs perpendicular to the longitudinal axis L of the optical assembly 12, the optical elements 18 are held by at least one region 26a, 26b, 26c functioning as a clamping mount for the optical elements 18.

The region 26a, 26b, 26c of the objective tube 16 functioning as a clamping mount is manufactured at least sectionally from a shape-memory material. For example, a shape-memory alloy or shape-memory polymer is provided as the shape-memory material. The shape-memory material can be a shape-memory alloy or shape-memory metal such as Nitinol is used.

The region 26a, 26b, 26c of the objective tube 16 functioning as a clamping mount completely encloses the optical element 18 along a circumference of the objective tube 16. In the depicted exemplary embodiment, a first region 26a functioning as a clamping mount, a second region 26b functioning as a clamping mount, and a third region 26c functioning as a clamping mount are provided. The regions 26a, 26b, 26c each have the shape of a hollow cylinder and completely enclose the associated optical element in a plane. This plane lies perpendicular to the direction of the longitudinal axis L which is oriented parallel to the optical axis of the optical system. The regions 26a, 26b, 26c of the objective tube 16 can be manufactured entirely from a shape-memory material.

In the depicted exemplary embodiment, the objective tube 16 comprises several optical elements 18, i.e., the lens groups 20a, 20b, 20c. For example, the first region 26a encloses the proximal lens group 20a as a first optical element 18, the second region 26b encloses the central lens group 20b as a second optical element 18, and the third region 26c encloses the distal lens group 20c as a third optical element 18. The central lens group 20b between the proximal and distal lens group 20a, 20c is alternatively held by the aperture tubes 24.

FIG. 2 shows the objective tube 16 in a deformed shape in which the objective tube 16 has a circular cross-section. By a subsequent temperature treatment above a memory temperature, the objective tube 16, or more precisely these regions 26a, 26b, 26c, change into a trained shape.

In the context of the present description, a trained shape is to be understood as the shape of the shape-memory material into which it is brought when it is heated to a correspondingly high temperature above the memory temperature. A deformed shape is the shape into which the material is brought by being deformed below a critical temperature so that training of this shape does not occur. The memory effect occurs from the deformed shape to the trained shape when the memory temperature is exceeded.

The trained shape of the objective tube 16 is selected so that a clamping seat is provided between the optical element 18 to be held and the region 26a, 26b, 26c of the objective tube 16 functioning as a clamping mount. The geometry and dimensions of the trained shape ensure that the optical elements 18 are held by an adequate clamping force which is accordingly neither too high or too low.

Contrary to the depiction in FIG. 2, the objective tube 16 is moreover provided to accommodate optical elements 18 with different cross-sections, in particular optical elements 18 with different diameters. In other words, it is necessary for the regions 26a, 26b, 26c in the state in which they provide the clamping seat for the optical element 18 to also have different cross-sections, in particular different diameters. For this purpose, there are transition regions between the regions 26a, 26b, 26c. The transition regions are deformable, such as plastically and/or elastically deformable. For example, spring elements are provided as the deformable transition region.

Figure 3A:
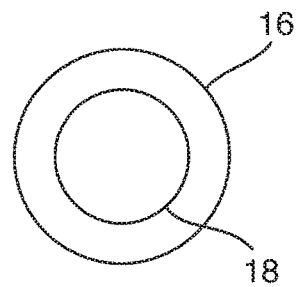
FIGS. 3a, 3b and FIGS. 4a, 4b illustrate schematically simplified cross-sectional views of an objective tube in a deformed shape and trained shape.
Figure 3B:
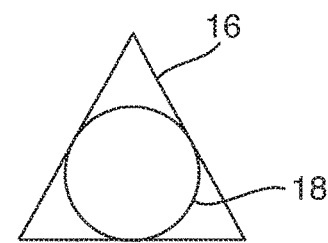

In a schematically simplified cross-sectional view, FIGS. 3a and 3b show an objective tube 16 in its deformed shape (FIG. 3a) and in its trained shape (FIG. 3b). For example, the objective tube 16, or more precisely its regions 26a, 26b, 26c, has a trained shape that is triangular viewed in the cross-section of the objective tube 16.

In the deformed shape, the optical element 18 is inserted in the objective tube 16. Then at least the regions 26a, 26b, 26c, including the entire objective tube 16 including the optical elements 18, are brought to a temperature above the memory temperature of the shape-memory material used for the regions 26a, 26b, 26c. The shape-memory material returns to its trained shape (FIG. 3b). The wall of the objective tube 16 comes into contact with the optical element 18 to create a clamping seat for the optical element 18. According to the exemplary embodiment depicted in FIG. 3, the optical element 18 is held at three points along its circumference. This creates a seat that is free of play and therefore particularly precise and secure for the optical element 18 in the objective tube 16. Along its circumference, the optical element 18 comes to rest in the middle of each side of the triangular objective tube 16 viewed in a cross-section.

Figure 4A:
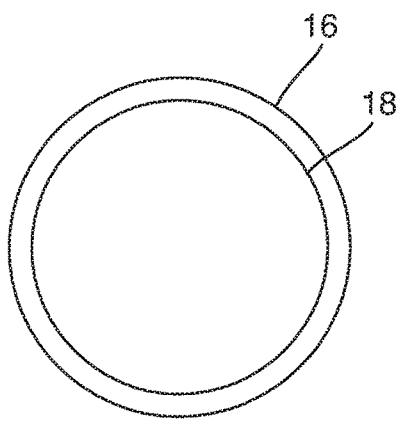
Figure 4B:
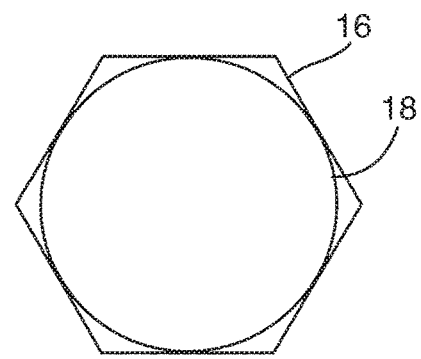

In another schematically simplified cross-sectional view, FIGS. 4a and 4b show an objective tube 16 in its deformed shape (FIG. 4a) and in its trained shape (FIG. 4b). In the trained shape, the objective tube 16 has a hexagonal cross-section according to this exemplary embodiment. Again, the optical element 18 comes into contact with the middle of each side of this hexagon along its circumference. With a six-sided cross-section to adjust to the position of the optical element 18, crossbars can be inserted in the objective tube 16, or more precisely in its regions 26a, 26b, 26c, that are removed after the clamping seat of the optical element 18 is achieved in the objective tube 16.

Figure 5A:
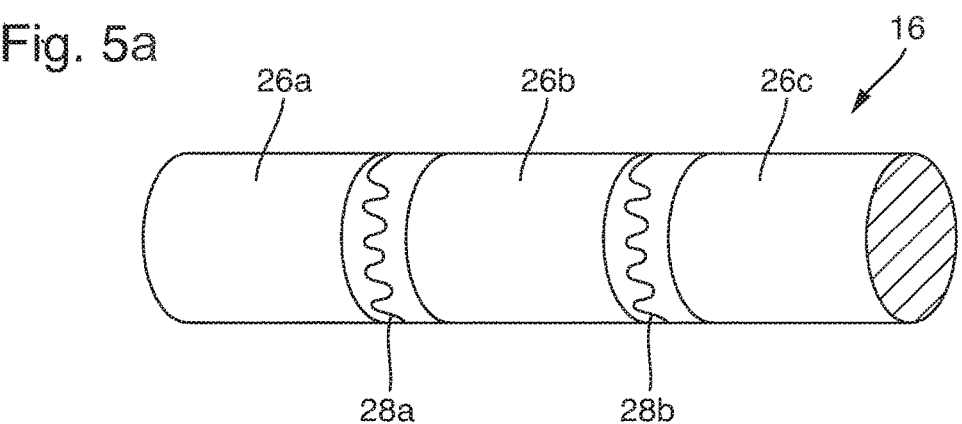
FIG. 5a illustrates a schematically simplified and perspective view of an objective tube.
Figure 5B:
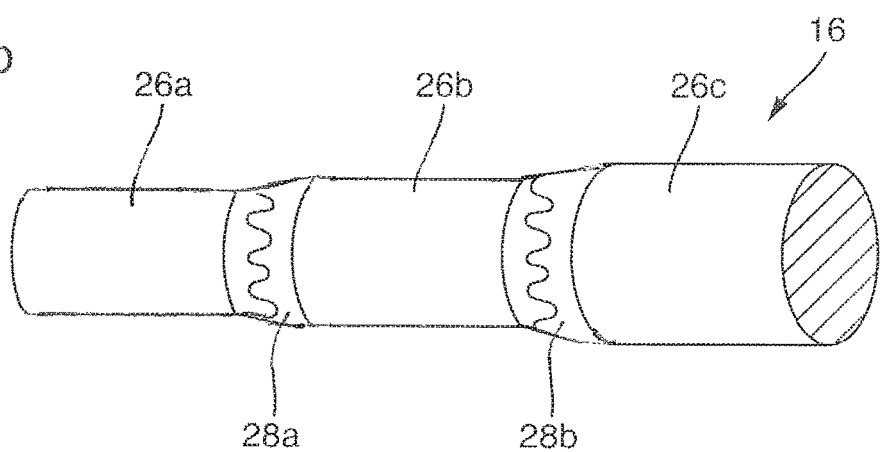
FIG. 5b illustrates a schematically simplified and perspective view of a modified objective tube.

In a schematic, simplified and perspective cross-sectional view, FIG. 5a shows an objective tube 16 comprising three regions 26a, 26b, 26c, between which there are two transition regions 28a, 28b. For example, the first transition region 28a that is arranged between the first region 26a and the second region 26b are spring elements. These are able to elastically deform and thereby compensate for different cross-sections of the first and second region 26a, 26b, such as different diameters of these regions 26a, 26b. The same holds true for the second transition region 28b that is arranged between the second region 26b and the third region 26c. In this regard, as shown in FIG. 5b, the transition regions 28a, 28b, can transition between regions 26a, 26b, 26c having different cross-sections, such as different shapes and/or sizes.

To manufacture an optical assembly 12 such as an endoscope objective 6, the following method can be pursued according to one exemplary embodiment: First, an objective tube 16 is provided that comprises at least one region 26a, 26b, 26c functioning as a clamping mount for the optical element 18. Such region 26a, 26b, 26c is at least sectionally manufactured from a shape-memory material, such as a shape-memory metal like Nitinol. The region 26a, 26b, 26c can be completely made of a shape-memory material. Then at least one optical element 18 such as a lens group 20a, 20b, 20c, which can each have multiple optical elements 18, such as the three lens groups 20a, 20b, 20c, is inserted in the objective tube 16. By then heating at least the regions 26a, 26b, 26c, or heating the entire objective tube 16 including the inserted optical elements 18, to a temperature above the memory temperature of the employed shape-memory material, a clamping seat is provided between the region 26a, 26b, 26c functioning as a clamping mount and the optical element 18.

With the assistance of the objective tube 16, that can be manufactured using a shape-memory material, the optical element(s) 18 can be precisely accommodated in the objective tube 16. Thus, the necessity of providing additional measures for fixing the optical elements 18, such as adhesive, can be avoided. The optical elements 18 can be accommodated in the optical tube 16 precisely enough in the objective to satisfy the high optical requirements for adjusting the optical system. The provided optical unit 12, such as the endoscope objective 6, can be suitable for detecting high-resolution image information (HD, ultra HD, 4K and higher).

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

REFERENCE NUMBER LIST

2 Endoscope
4 Distal end
6 Endoscope objective
8 Shaft
10 Handle
12 Optical assembly
14 Protective disc
16 Objective tube
18 Optical element
20a Proximal lens group
20b Central lens group
20c Distal lens group
22 End stop
24 Aperture tube
26a First region
B2 Second region
26c Third region
28a First transition region
28b Second transition region
R Radial direction
L Longitudinal direction

What is claimed is:

1. An optical assembly for an endoscope, the optical assembly comprising:
  an objective tube; and
  at least one optical element held in the objective tube;
  wherein the objective tube comprises at least one region acting as a clamping mount for the at least one optical element; and
  the at least one region of the objective tube acting as the clamping mount is at least sectionally formed of a shape-memory material configured to exhibit a shape memory effect upon heating above a memory temperature which changes a shape of the at least one region of the objective tube acting as a clamping mount so as to clamp the at least one optical element in the objective tube.

2. The optical assembly according to claim 1, wherein the at least one region of the objective tube acting as a clamping mount fully encloses the optical element along a circumference of the objective tube.

3. The optical assembly according to claim 2, wherein the at least one region is completely formed of the shape-memory material.

4. The optical assembly according to claim 1, wherein the at least one optical element comprises a first optical element and a second optical element, the first optical element being held in a first region of the objective tube acting as a clamping mount for the first optical element and the second optical element being held in a second region of the objective tube acting as a clamping mount for the second optical element, wherein the objective tube comprises a deformable transition region between the first region and the second region.

5. The optical assembly according to claim 4, wherein the first region has a first cross-section and the second region has a second cross-section different from the first cross-section, wherein the deformable transition region transitions from the first cross-section to the second cross-section.

6. The optical assembly according to claim 5, wherein the first cross-section is a first diameter and the second cross-section is a second diameter, the deformable transition region transitioning from the first diameter to the second diameter.

7. The optical assembly according to claim 6, wherein a deformed shape of the objective tube is circular in at least the one region acting as the clamping mount.

8. The optical assembly according to claim 1, wherein the at least one region of the objective tube acting as the clamping mount has a trained shape which is polygonal when viewed in a cross-section of the objective tube.

9. The optical assembly according to claim 1, wherein the shape-memory material is at least one of a shape-memory alloy and a shape-memory polymer.

10. An endoscope comprising the optical assembly according to claim 1 as one of an endoscope objective or relay lens.

11. The endoscope according to claim 10, wherein the at least one optical element is a lens.

12. A method for producing an optical assembly, the method comprising:
  providing an objective tube having at least one region acting as a clamping mount for at least one optical element, the at least one region being at least sectionally formed from a shape-memory material;
  inserting the at least one optical element into the at least one region of the objective tube acting as the clamping mount; and
  heating the at least one region of the objective tube acting as the clamping mount to a temperature above a memory temperature of the shape-memory material to change a shape of the at least one region of the objective tube acting as a clamping mount so as to clamp the at least one optical element in the objective tube.

* * * * *